Figure 1:
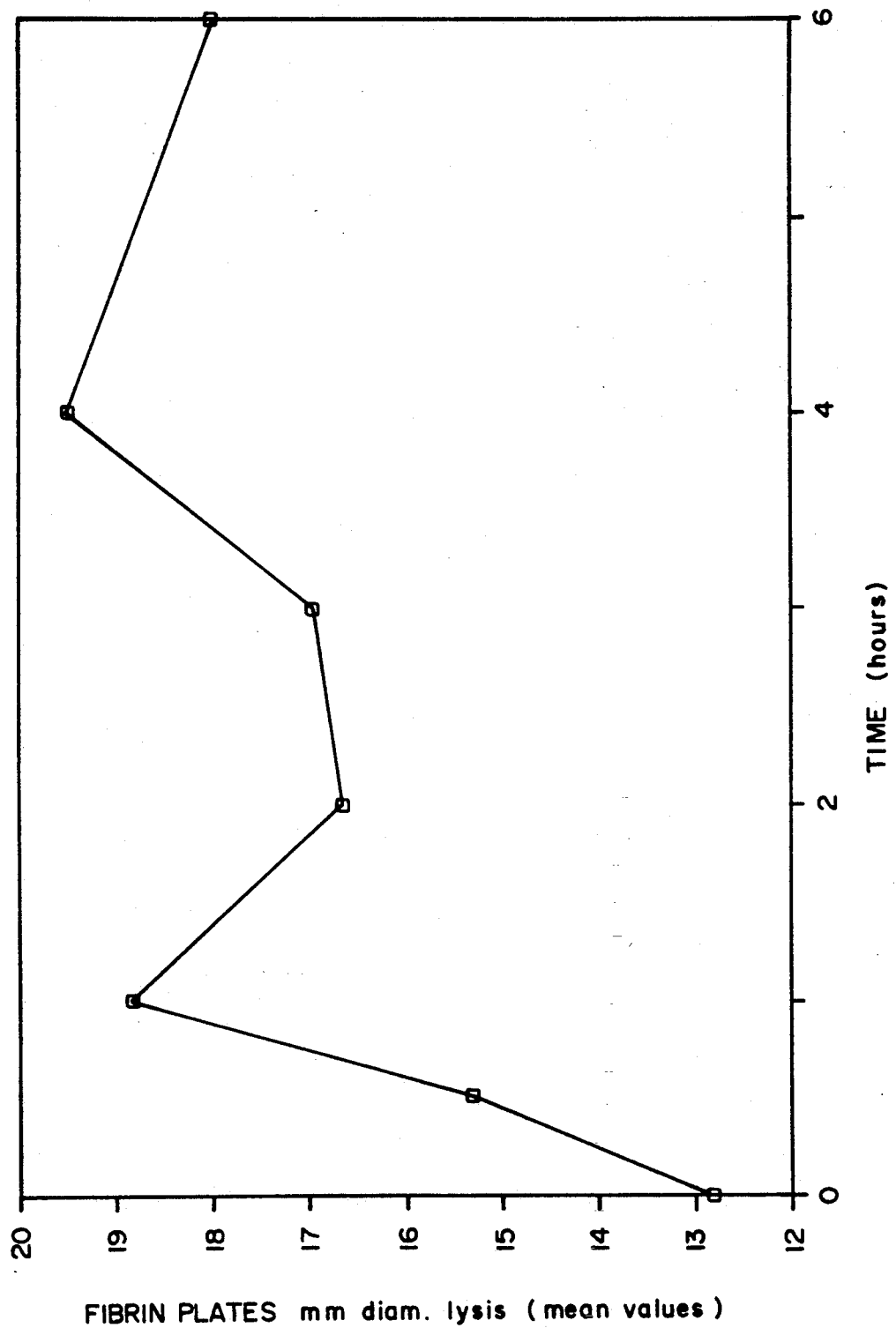

United States Patent [19]

Cristofori et al.

[11] Patent Number: 5,252,339

[45] Date of Patent: Oct. 12, 1993

[54] PHARMACEUTICAL COMPOSITIONS CONTAINING ORALLY ABSORBABLE GLYCOSAMIMOGLYCANS

[75] Inventors: Manlio Cristofori, Bologna; Egidio Marchi, Casalecchio de Reno; Leone G. Rotini, Bologna, all of Italy

[73] Assignee: ALFA Wasserman s.p.A., Alanno Scalo, Italy

[21] Appl. No.: 821,455

[22] Filed: Jan. 15, 1992

[30] Foreign Application Priority Data

Jan. 30, 1991 [IT] Italy .................. B091A000024

[51] Int. Cl.⁵ ............................................. A61K 9/36
[52] U.S. Cl. ........................... 424/479; 424/465; 424/474; 424/482; 424/490; 424/493; 424/497; 424/498; 424/499; 424/502
[58] Field of Search ............... 424/490, 493, 497, 498, 424/499, 502, 465, 474, 479, 482; 514/54, 56, 62

[56] References Cited

U.S. PATENT DOCUMENTS

| | | | |
|---|---|---|---|
| 3,482,014 | 12/1969 | Koh | 514/56 |
| 3,506,642 | 4/1970 | Koh | 260/209 |
| 3,548,052 | 12/1970 | Yan Koh | 424/16 |
| 3,574,832 | 4/1971 | Engel | 514/56 |
| 3,577,534 | 5/1971 | Koh et al. | 514/56 |
| 4,510,135 | 4/1985 | Teng | 514/56 |
| 4,604,376 | 8/1986 | Teng | 514/4 |
| 4,654,327 | 3/1987 | Teng | 514/56 |
| 5,032,405 | 7/1991 | Huang | 424/474 |
| 5,102,788 | 4/1992 | Cole | 435/188 |

FOREIGN PATENT DOCUMENTS

| | | |
|---|---|---|
| 827595 | 7/1975 | Belgium . |
| 860011 | 4/1978 | Belgium . |
| 2745943 | 4/1978 | Fed. Rep. of Germany . |
| 3331009 | 3/1985 | Fed. Rep. of Germany . |
| 2492259 | 4/1982 | France . |
| 1157754 | 7/1969 | United Kingdom . |
| 2131691 | 6/1984 | United Kingdom . |
| 8505362 | 12/1985 | World Int. Prop. O. . |

OTHER PUBLICATIONS

Can. J. Biochem., 47, 951–4, (1969).
Can J. Physiol. Pharmacol., 54, (4), 613–7, (1976).
Chem. Pharm. Bull., 30, (6), 2245–7, (1982).
J. Pharm. Sci., 58, 706–10, (1969).
J. Pharm. Sci., 58, 1372–5, (1969).
Proc. Soc. Exp., Biol. Med., 111, 713–5 (1962).
Throm. Diath., Haemorrh., 25, 187–200, (1971).

Primary Examiner—Thurman K. Page
Assistant Examiner—G. S. Kishore
Attorney, Agent, or Firm—Bucknam and Archer

[57] ABSTRACT

Pharmaceutical compositions for oral use, preferably selected from capsules, tablets or sugar coated tablets, coated by an enterosoluble gastroresistant film, containing a lyophilizate consisting of therapeutically effective amounts of a glycosaminoglycan, a thickening substance and surfactants, and process for obtaining them. The compositions make possible the absorption of the orally administered glycosaminoglycans in the duodenum and in the intestine and the consequent performance of their anticoagulant, fibrinolytic, antithrombotic, antiatherosclerotic and antihyperlipoproteinemic properties.

9 Claims, 3 Drawing Sheets

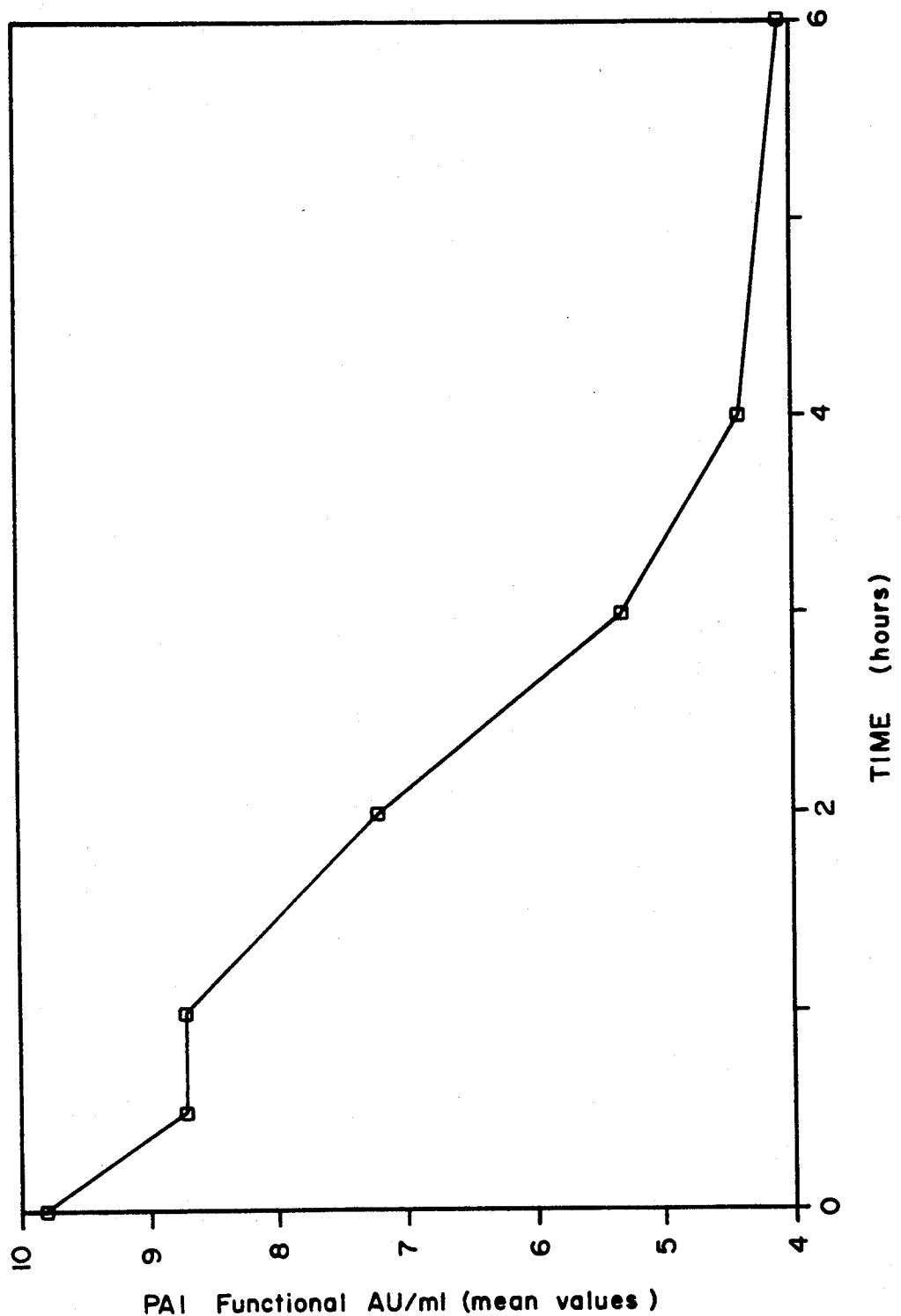

PHARMACEUTICAL COMPOSITIONS CONTAINING ORALLY ABSORBABLE GLYCOSAMIMOGLYCANS

BACKGROUND OF THE INVENTION

The glycosaminoglycans are products of natural origin, obtained from tissues of animal origin, made by heterogeneous mixtures of chains of polysaccharides sulfated in different ways, having a very wide range of molecular weights, comprised from few thousands and some tens of thousands of Daltons.

Heparin is the most known among them, mainly made by units containing D-glucosamine and L-iduronic or D-glucuronic acid sulfated in different ways, having a range of molecular weights comprised between about 6,000 and 30,000 Daltons, generally used as an anticoagulant and antithrombotic drug in the form of sodium, potassium, calcium or magnesium salts.

Low molecular weight heparins, derivatives having a lesser degree of polymerization, with molecular weights comprised between about 1,500 and about 8,000 Daltons, having therapeutical characteristics like those of the heparin, are obtained by means of enzymatic or chemical treatment.

The chondroitins are other kinds of glycosaminoglycans extracted from tissues of animal origin, and one of them, previously known as chondroitin sulfate B, is the dermatan sulfate having antithrombotic and antihyperlipoproteinemic activity.

Low molecular weight fractions, between about 2,000 and about 8,000 Daltons, can also be obtained from dermatan sulfate like it happens for heparin.

The glucuronylglycosaminoglycan sulfate known under the name of sulodexide (International Non-proprietary Name), endowed with antithrombotic and antiatherosclerotic activity, is another substance pertaining to this class of drugs.

All these glycosaminoglycans were widely studied in the prevention and treatment of many pathologies of thrombotic and atherosclerotic origin, in the form of salts of alkali or alkali-earth metals like sodium, potassium, calcium or magnesium. However, their therapeutic use is hindered by the fact that these salts are mainly administered by parenteral way because of their scarce oral absorption.

For quite a time many remarkable efforts are carried out in order to fine adjuvant substances or derivatives or pharmaceutical formulations suitable for increasing their oral bioavailability, due to the great therapeutic interest that the glycosaminoglycans have in the prevention and treatment of the atherosclerotic and thrombotic pathologies.

At the beginning they tried to solve the problem by adding to aqueous solutions of heparin adjuvant substances like EDTA [Tidball et al., Proc. Soc. Exp. Biol. Med., 111, 713-5 (1962)], dimethylsulfoxide and diethylsulfone [Koh T. Y., Can. J. Biochem., 47, 951-4, (1969)], nitrilotriacetic acid [Jarret et al., Thromb. Diath. Haemorrh., 25, 187-200, (1971)] or citric acid [Sue T. K. et al, Can. J. Physiol. Pharmacol., 54, (4) 613-7, (1976)].

Engel R. H. and Riggi S. J. tried to help the oral absorption of the heparin by directly introducing emulsions made by aqueous solutions of heparin, a vegetable oil and ionic or non ionic surfactants into the duodenum of the experimental animals [J. Pharm. Sci., 58, 706-10 and 1372-5, (1969)].

Belgian patent BE 827,595 and British patent GB 1,563,161 describe the preparation of anhydrous suspensions of glycosaminoglycans in an oily medium in the presence of an anionic surfactant and show their absorption in the rat by intraduodenal administration.

Another way was the preparation of salts and complexes with weakly basic organic substances, like amines, or with amphoteric substances, like amides or aminoacids, as shown by U.S. Pat. Nos. 3,506,642 and 3,577,534.

More recently, they tried to help the absorption by using suitable pharmaceutical formulations based on liposomes as vehicles for the glycosaminoglycans [Masaharu Ueno et al., Chem. Pharm. Bull., 30, (6), 2245-78, (1982), Belgian patent BE 860,011, French patent FR 2,492,259] or by doing some complexes with quaternary ammonium bases [International publication PCT WO 85/05,362, U.S. Pat. Nos. 4,510,135 and 4,654,327].

Notwithstanding all these attempts, the need of finding new kinds of oral pharmaceutical formulations containing glycosaminoglycans endowed with better bioavailability, still exists.

The present invention constitutes a valid answer to this problem; in fact it was discovered that orally administrable pharmaceutical compositions, for instance tablets, capsules or sugar coated tablets, coated with an enterosoluble gastroresistant film, containing a lyophilisate made by a mixture of a glycosaminoglycan with a thickening substance and surfactants, after having unaltered crossed the gastric juices, disintegrated in the duodenum and intestine by releasing the glycosaminoglycan whose absorption is helped by the presence of the thickening substance and of the surfactants present in the lyophilisate, as shown by the tests of fibrinolytic activity carried out in man.

SUMMARY OF THE INVENTION

Pharmaceutical compositions for oral use coated with an entersoluble gastroresistant film, containing a lyophilisate made by therapeutically effective amounts of a glycosaminoglycan, a thickening agent and surfactants are the object of the present invention.

Pharmaceutical compositions for oral use preferred in the fulfillment of the present invention are tablets, capsules and sugar coated tablets.

The process for obtaining said pharmaceutical compositions and their therapeutic use in the prevention and treatment of the thrombotic and atherosclerotic pathologies are also object of the present invention.

The scope of the present invention is the improvement or the oral absorption of the glycosaminoglycans so that, also through this way, the best performance of the anticoagulant, fibrinolytic, antithrombotic, antiatherosclerotic and antihyperlipoproteinemic activities of this class of drugs, whose therapeutic use is still carried out mainly through the parenteral way giving many inconveniences and disadvantages of practical and psychological nature caused by this kind of treatment.

The invention is based on the contemporary presence of two factors that help the stability and the absorption of the glycosaminoglycans:

a) enterosoluble gastroresistant coating of the pharmaceutical compositions that enables the active principle to unaltered cross the gastric juices, in which the glycosaminoglycans are not very much stable and are very poorly absorbed, and to be released into the duodenum and the intestine, in which the glycosaminoglycans are stable and can be better absorbed;

b) presence, in the lyophilisate containing the glycosaminoglycan, of a thickening substance and of surfactants that, released together with the glycosaminoglycan, considerably help the absorption of the active principle into the duodenum and the intestine.

The overall end result produced by these two factors is a good bioavailability of the glycosaminoglycans as clearly shown by some tests of fibrinolysis carried out in man.

The obtained experimental data clearly show the oral absorption in man of the pharmaceutical compositions described in the invention and therefore they allow the use of these compositions in the prevention and treatment of the thrombotic and atherosclerotic pathologies.

The therapeutic dosage preferred in the fulfillment of the present invention is comprised between 25 mg and 250 mg of glycosaminoglycan.

The preparation of the lyophilisate containing the glycosaminoglycan as active principle, together with a thickening substance and surfactants as adjuvants of the absorption is the first step in preparing the pharmaceutical forms for oral use object of the present invention. The thickening agent is dissolved under heating and stirring in distilled water and subsequently the surfactants are dissolved. The solution, after cooling to room temperature, is added to an aqueous solution of glycosaminoglycan and the resulting solution is freeze-dried and the obtained lyophilisate is pulverized.

All the glycosaminoglycans endowed with therapeutic activity can be used in the fulfillment of the present invention; heparin and its alkali and alkali-earth salts, fractions of low molecular weight heparin obtained according to well known methods of enzymatic or chemical depolymerization, dermatan sulfate and its low molecular weight fractions and the glucuronyl-glycosaminoglycan sulfate known under the name of sulodexide (International Non-proprietary Name) are preferred among them.

Many thickening substances can be advantageously used in the fulfillment of the present invention. They pertain to many chemical classes, for instance those of the modified or unmodified natural polymers, of the carboxyl and vinyl polymers, of the esters of the fatty acids, of the aluminium oxides and of the silicic anhydrides. Gum arabic, tragacanth, xanthan gum, pectins, starchs, carrageenans, alginates, gelatin and casein from the natural polymers, hydroxyethylcellulose, methylcellulose, hydroxypropylcellulose and carboxymethylcellulose from the modified natural polymers, polyvinylpyrrolidone and polyvinylic alcohol from the vinyl polymers, Carbopol ® from the carboxyvinyl polymers, hydrogenated castor oil named Cutina ® HR from the esters of fatty acids and aluminium oxide monostearate from the aluminium oxides are preferred in the fulfillment of the present invention.

Both the anionic surfactants, like the alkali salts of bile acids, of carboxylic and sulfonic organic acids and of alkyl and aryl sulfates, and the amphoteric surfactants, like the phospholipids of natural origin, like the lecithins of both vegetal and animal origin, and the betaines, and the non-ionic surfactants like the esters of mono and di-saccharides with fatty acids, the polyoxyethylenic alcohols and the esters of fatty acids with the polyoxyethylenic acids can be advantageously used as surfactants.

Sodium cholate, sodium glycholate, sodium taurocholate, sodium laurylsarcosinate, egg lecithin, soja bean lecithin, saccharose monopalmitate and polysorbates known as Tween ® are the surfactants preferred in the fulfillment of the present invention.

The preparation of the enterosoluble gastroresistant pharmaceutical compositions for oral use containing the above described lyophilisate is the second step of the process.

Said compositions can be in the form of capsules, tablets or sugar coated tablets and their distinctive characteristic is the coating with an enterosoluble gastroresistant film which enables the active principle to unaltered cross the gastric juices and to be dissolved into the duodenal and intestinal zones so allowing the absorption of the active principle helped by the presence of the thickening substance and of the surfactants.

The different pharmaceutical forms for oral use not coated by the protective film are prepared according to known methods. For instance the tablets are prepared by dry granulating the lyophilisate, containing active principle, thickening agent and surfactants, mixed with excipients like maize starch and lactose. The so obtained granulate is mixed with other excipients like microgranular cellulose, reticulated polyvinylpyrrolidone and magnesium stearate and then is compressed in order to obtain a normal tablet.

The capsules are prepared by dividing the lyophilisate, alone or together with excipients, like for instance an oily substance made by a mixture of caprilo-capric glycerides, in capsules of soft or hard gelatin that are subsequently sealed up.

The tablets or capsules obtained with known methods, are submitted to the gastroprotective treatment. In case the sugar coated tablets are the pharmaceutical form, the tablets are submitted to sugar coating according to known methods, after the gastroprotective treatment.

The tablets or capsules obtained with known methods, are submitted to the gastroprotective treatment.

A first, non-protective, coating, that serves as support to obtain an optimal distribution of the protective gastroresistant enterosoluble film on the pharmaceutical form, is carried out before putting into effect the coating by means of the gastroresistant enterosoluble film.

This non-protective coating is carried out by spraying on the pharmaceutical forms in coating pan a suspension made by hydroxypropylmethylcellulose, polyethylene glycol 6000, titanium dioxide and talc in a 22:1 mixture of 95% ethyl alcohol and water, in such an amount that the weight of this first film is comprised between 1% and 5% as to the weight of the non-coated form.

This first film is then covered by the gastroresistant enterosoluble film. Many coating substances can advantageously be used to obtain a gastroresistant enterosoluble coating. The coating substances preferred in the fulfillment of the present invention are cellulose acetate, the copolymers of the methacrylic acid and of the methacrylic esters in different ratios, commercially known under the trademark Eudragit ®, polyvinylacetophthalate and hydroxypropylmethylcellulose phthalate.

An amount of plasticizers comprised between 5% and 15% in weight as to the weight of coating agent is added to give optimal elasticity and flexibility to the gastroresistant enterosoluble film. The plasticizers preferred in the fulfillment of the present invention are diethylphthalate, triacetin, polyethylenglycols and acetylated monoglycerides, alone or in admixture among them.

The application of the gastroresistant enterosoluble film is carried out by dissolving one or more coating substances together with one or more plasticizers in a 80:1 mixture of ethyl alcohol and water and spraying this solution in coating pan on the pharmaceutical forms previously coated with the non-protective coating, in such an amount that the weight of the gastroresistant enterosoluble film is comprised between 2% and 10% as to the weight of the non-coated pharmaceutical form.

The so obtained gastroresistant enterosoluble pharmaceutical forms make possible the absorption of the glycosaminoglycans they contain as it is clearly shown by some tests on the fibrinolytic activity exercised in man by two tablets prepared according to example 5, each containing 100 mg of glucuronylglycosaminoglycan sulfate known as sulodexide (INN) as active principle. Two gastroresistant enterosoluble tablets prepared according to example 5, each containing 100 mg of sulodexide, were orally administered to six healthy volunteers fasting from 8 hours. Drawings of citrated blood were carried out immediately before the administration and 0.5, 1, 2, 3, 4 and 6 hours after the administration of the tablets. The samples of blood were centrifuged at 4500 rpm for 10 minutes and the following parameters were examined on the obtained plasma for the evaluation of the fibrinolytic activity, one of the characteristic activities of the sulodexide:

a) fibrin plates (method of Haverkate F. et al.);
b) inhibitor of the activator of the plasminogen as concentration: PAI-1 antigen (analytic kit by Ortho);
c) inhibitor of the activator of the plasminogen as activity with a functional test: PAI (analytic kit by Ortho).

FIG. 1—is a plot of the fibrin plates on the ordinate, and time on the abscissa, determined by the Haverkate et al method and shows the lysis of the euglobulinic fraction which contains the activator of the plasminogen of the plasma on plates of human fibrin.

Figure 2:
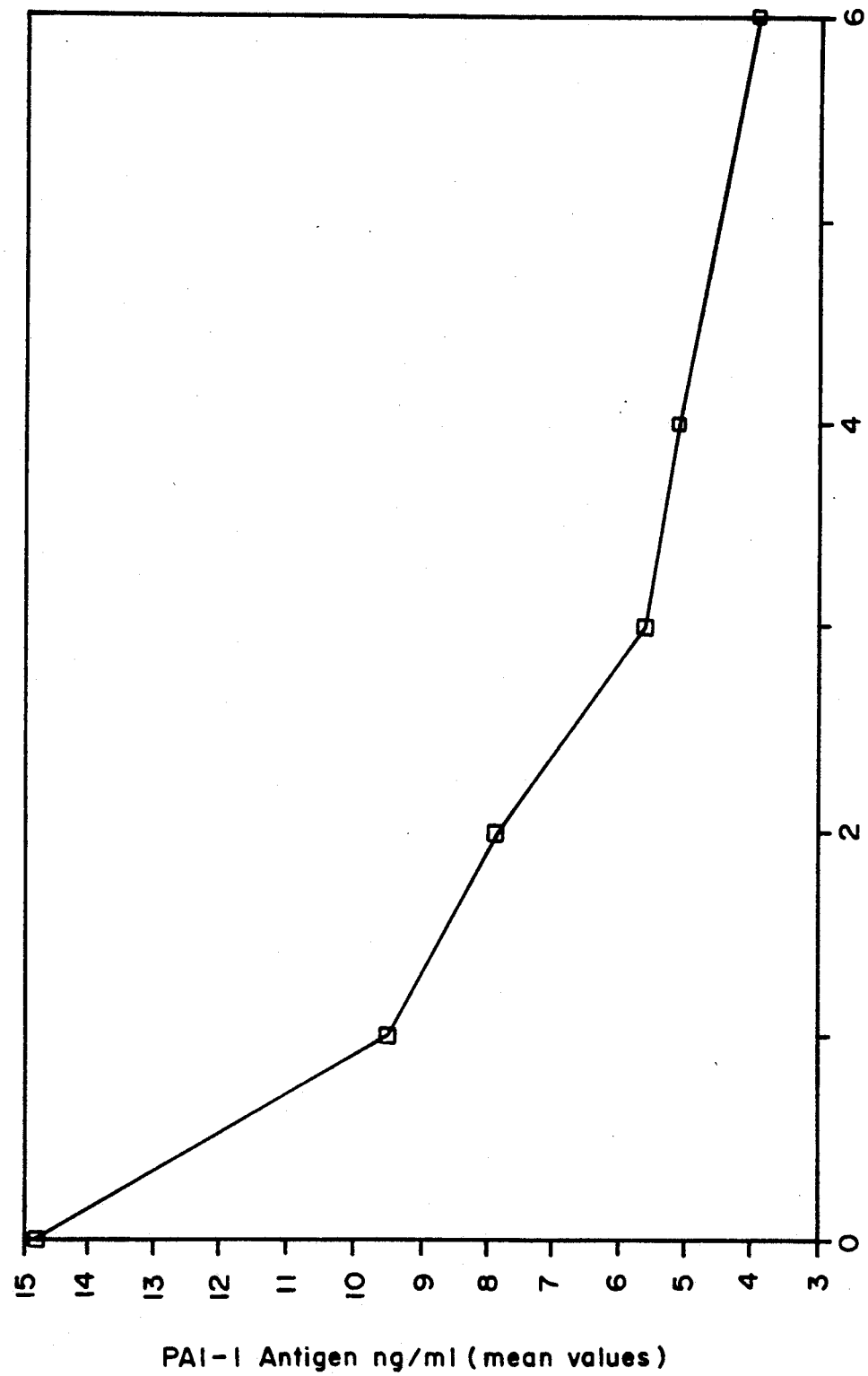

FIG. 2—shows the concentration of the activator of the plasminogen, antigen ng/ml with time.

FIG. 3—is a plot of the activity of the inhibitor of the activator of the plasminogen on the ordinate with time on the abscissa determined by means of a functional test.

Method a) mainly shows the activity of the activator of the plasminogen and was carried out according to the method described by Haverkate F. et al. in "Progress in chemical fibrinolysis and thrombolysis", J. F. Davidson, M. M. Samama, P. C. Desnoyers Editors, Vol. 1, pp 151-7, (1975), Raven Press Publ. N.Y., which evaluates the lysis of the euglobulinic fraction mainly containing the activator of the plasminogen of the plasma on plates of human fibrin. Method b), carried out according to the method ELISA, shows the inhibitor of the activator of the plasminogen as concentration, while method c), based on the measurement of the amidolytic activity of plasmin produced on a chromogenic substrate, shows the activity of the inhibitor of the activator of the plasminogen by means of a functional test.

The tests were carried out according to the way described in the analytic kit of the firm Ortho.

The experimental results summarized in the following table 1 and in the graphs of FIGS. 1, 2 and 3, clearly show the absorption of the orally administered sulodexide by means of one of the pharmaceutical formulations object of the invention. In fact the experimental data already show the fibrinolytic effect of the sulodexide one hour after the administration. This effect is very manifest and lasts until the end of the drawings effected in the test (6 hours). Moreover a good mutual relation exhists between the values of the inhibitor of the activator of the plasminogen and the corresponding values of the activator of the plasminogen with plates of fibrin.

TABLE 1

Fibrinolytic activity in man of 200 mg of sulodexide orally administered by means of the pharmaceutical formulation described in Example 5 ($x \pm s.e.$)

| TIME (hours) | FIBRIN PLATES (mm diam. lysis) | PAI-1 ANTIGEN (ng/ml) | PAI FUNCTIONAL (AU/ml) |
|---|---|---|---|
| 0 | 12.9 ± 1.0 | 14.8 ± 3.0 | 9.8 ± 2.3 |
| 0.5 | 15.3 ± 0.6 | n.d. | 8.7 ± 3.1 |
| 1 | 18.9 ± 1.3 | 9.5 ± 2.6 | 8.7 ± 3.6 |
| 2 | 16.7 ± 1.1 | 7.9 ± 2.5 | 7.2 ± 2.4 |
| 3 | 17.0 ± 1.5 | 5.6 ± 1.8 | 5.3 ± 2.0 |
| 4 | 19.4 ± 0.7 | 5.1 ± 1.4 | 4.4 ± 1.2 |
| 6 | 18.0 ± 0.7 | 3.9 ± 0.9 | 4.1 ± 1.4 | n.d. = not determined
diam. = diameter

The following glycosaminoglycans were used in the examples described in the present invention:

Injectable sodium heparin supplied by the firm OPOCRIN (Italy), having an anticoagulant activity equal to 168 I.U./mg;

low molecular weight heparin, supplied by the firm OPOCRIN (Italy), obtained by depolymerization of heparin in the presence of cupric acetate and of hydrogen peroxide, as described in european publication EP 0121067, having an average molecular weight equal to 4500 Daltons and an anticoagulant activity equal to 46 USP/mg and 202 I.U. AXa/mg;

glucuronylglycosaminoglycan sulfate known under the name sulodexide (INN), supplied by ALFA WASSERMANN S.p.A. (Italy), having a title equal to 37 I.U. APTT/mg and to 82 I.U. AXa/mg;

low molecular weight dermatan sulfate supplied by the firm OPOCRIN (Italy), having an average molecular weight equal to 5600 Daltons and a title equal to 1.4 I.U. APTT/mg and to 10 I.U. AXa/mg.

The following examples have to be considered only as a further explanation and illustration and not as a limitation of the present invention.

EXAMPLE 1

Lyophilisate containing glucuronylglycosaminoglycan sulfate (sulodexide)

100 Milligrams of xanthan gum are put into 100 ml of distilled water while heating under stirring until complete solubilization, subsequently 250 mg of saccharose monopalmitate and 250 mg of sodium laurylsarcosinate are added and dissolved. The solution is cooled to room temperature and is added with a solution containing 500 mg of glucuronylglycosaminoglycan sulfate in 20 ml of distilled water. The resulting solution is freeze-dried and the obtained lyophilisate is pulverized in mortar.

EXAMPLE 2

Lyophilisate containing low molecular weight dermatan sulfate

200 Milligrams of sodium alginate are put into 100 ml of distilled water while heating under stirring until complete solubilization, subsequently 1000 mg of saccharose monopalmitate and 500 mg of sodium laurylsarcosinate are added and dissolved. The solution is cooled to room temperature and is added with a solution containing 2000 mg of low molecular weight dermatan sulfate in 20 ml of distilled water. The resulting solution is freeze-dried and the obtained lyophilisate is pulverized in mortar.

EXAMPLE 3

Lyophilisate containing sodium heparin

The above lyophilisate is obtained by working as in example 1 and using 500 mg of sodium heparin instead of the corresponding amount of glucuronylglycosaminoglycan sulfate.

EXAMPLE 4

Lyophilisate containing low molecular weight heparin

The above lyophilisate is obtained by working as in example 1 and using 500 mg of low molecular weight heparin instead of the corresponding amount of glucuronylglycosaminoglycan sulfate.

EXAMPLE 5

Gastroresistant tablets containing glucuronylglycosaminoglycan sulfate (sulodexide)

| Composition of each tablet | |
|---|---|
| Glucuronylglycosaminoglycan sulfate | 100 mg |
| Saccharose monopalmitate | 50 mg |
| Sodium laurylsarcosinate | 50 mg |
| Xanthan gum | 20 mg |
| Maze starch | 93.8 mg |
| Lactose | 81.5 mg |
| Microgranular cellulose | 300 mg |
| Reticulated polyvinylpyrrolidone | 100 mg |
| Magnesium stearate | 10 mg |
| Hydroxypropylmethylcellulose | 14 mg |
| Polyethylene glycol 6000 | 0.8 mg |
| Titanium dioxide | 3.2 mg |
| Talc | 3.2 mg |
| Hydroxypropylmethylcellulose phthalate | 32 mg |
| Acetylated monoglycerides | 3.2 mg |

One thousand tablets are obtained by using 220 g of lyophilisate prepared according to example 1. Said lyophilisate is mixed together with maize starch and lactose and the mixture is dry granulated and sifted on a sieve having meshes equal to 0.8 mm. The so obtained granulate is mixed together with microgranular cellulose, reticular polyvinylpyrrolidone and magnesium stearate and the resulting mixture is tabletted. The tablets are coated in coating pan by means of a first film made by a suspension of hydroxypropylmethylcelluose, polyethylene glycol 6000, titanium dioxide and talc in a 22:1 mixture of 95% ethyl alcohol and water. Subsequently the gastroresistant enterosoluble coating is carried out by spraying in the coating pan a solution of hydroxypropylemethylcellulose phthalate and acetylated monoglycerides in a 80:1 mixture of ethyl alcohol and water on the tablets coated with the first film.

EXAMPLE 6

Gastroresistant soft gelatin capsules containing glucuronylglycosaminoglycan sulfate (sulodexide)

| Composition of each capsule | |
|---|---|
| Glucuronylglycosaminoglycan sulfate (sulodexide) | 100 mg |
| Saccharose monopalmitate | 50 mg |
| Sodium laurylsarcosinate | 50 mg |
| Xanthan gum | 20 mg |
| Caprilo-capric glycerides | 380 mg |
| Hydroxypropylmethylcellulose | 10.5 mg |
| Polyethylene glycol 6000 | 0.6 mg |
| Titanium dioxide | 2.4 mg |
| Talc | 2.4 mg |
| Hydroxypropylmethylcellulose phthalate | 24 mg |
| Acetylated monoglycerides | 2.4 mg |

200 Grams of lyophilisate prepared according to example 1 are mixed with 380 g of caprilo-capric glycerides. The mixture is made homogeneous in a cylinder-mill and then is shared in 1000 soft gelatin type 10 oval capsules. These capsules are first coated in coating pan with a first film made by hydroxypropylmethylcellulose, polyethylene glycol 6000, titanium dioxide and talc suspended in a 22:1 mixture of 95% ethyl alcohol and water. The gastroresistant enterosoluble coating is subsequently carried out by spraying in the coating pan a solution of hydroxypropylmethylcellulose phthalate and acetylated monoglycerides in a 80:1 mixture of ethyl alcohol and water on the capsules coated with the first film.

EXAMPLE 7

Gastroresistant hard gelatin capsules containing low molecular weight dermatan sulfate

| Composition of each capsule | |
|---|---|
| Low molecular weight dermatan sulfate | 200 mg |
| Saccharose monopalmitate | 100 mg |
| Sodium laurylsarcosinate | 50 mg |
| Sodium alginate | 20 mg |
| Hydroxypropylmethylcellulose | 10.5 mg |
| Polyethylene glycol 6000 | 0.6 mg |
| Titanium dioxide | 2.4 mg |
| Talc | 2.4 mg |
| Hydroxypropylmethylcellulose phthalate | 24 mg |
| Acetylated monoglycerides | 2.4 mg |

370 Grams of lyophilisate prepared according to example 2 are shared in 1000 hard gelatin type O capsules that are sealed up by means of a 31% (w/v) aqueous gelatin solution and then are coated in coating pan by means of a first film made by hydroxypropylmethylcellulose, polyethylene glycol 6000, titanium dioxide and talc suspended in a 22:1 mixture of 95% ethyl alcohol and water. Subsequently the gastroresistant enterosoluble coating is carried out by spraying in the coating pan a solution of hydroxypropylmethylcellulose phthalate and acetylated monoglycerides in a 80:1 mixture of ethyl alcohol and water on the capsules coated with the first film.

EXAMPLE 8

Gastroresistant sugar coated tablets containing low molecular weight heparin

| Composition of each sugar coated tablet | |
|---|---|
| Low molecular weight heparin | 50 mg |
| Saccharose monopalmitate | 25 mg |
| Sodium laurylsarcosinate | 25 mg |
| Xanthan gum | 10 mg |
| Maize starch | 17 mg |
| Lactose | 41 mg |
| Microgranular cellulose | 150 mg |

| Composition of each sugar coated tablet (continued) | |
| --- | --- |
| Reticulated polyvinylpyrrolidone | 50 mg |
| Magnesium stearate | 5 mg |
| Hydroxypropylmethylcellulose | 7 mg |
| Polyethylene glycol 6000 | 0.4 mg |
| Titanium dioxide | 6.4 mg |
| Talc | 5.8 mg |
| Hydroxypropylmethylcellulose phthalate | 16 mg |
| Acetylated monoglycerides | 1.6 mg |
| Gum arabic | 7 mg |
| Saccharose | 138 mg |
| Carnauba wax | 0.2 mg |
| White wax | 0.1 mg |

One thousand sugar coated tablets are obtained by using 110 g of lyophilisate prepared according to example 4. Said lyophilisate is mixed with maize starch and lactose and the resulting mixture is dry granulated and sifted on a sieve having meshes of 0.8 mm. The obtained granulate is mixed with microgranular cellulose, reticulated polyvinylpyrrolidone and magnesium stearate and the mixture is tabletted. The obtained tablets are coated in coating pan with a first film made by a mixture containing 7 g of hydroxypropylmethylcellulose, 0.4 g of polyethylene glycol 6000, 1.6 g of titanium dioxide and 1.6 g of talc suspended in a 22:1 mixture of 95% ethyl alcohol and water. Subsequently the gastroresistant enterosoluble coating is carried out by spraying in the coating pan a solution of hydroxypropylmethylcellulose phthalate and acetylated monoglycerides in a 80:1 mixture of ethyl alcohol and water on the tablets coated by the first film. The so obtained gastroresistant enterosoluble tablets are then submitted to the sugar coating by using an aqueous suspension containing 138 g of saccharose, 7 g of gum arabic, 4.8 g of titanium dioxide and 4.2 g of talc. The sugar coated tablets are then polished by using a solution of carnauba wax and white wax in chloroform.

EXAMPLE 9

Gastroresistant tablets containing sodium heparin

| Composition of each tablet | |
| --- | --- |
| Sodium heparin | 100 mg |
| Saccharose monopalmitate | 50 mg |
| Sodium laurylsarcosinate | 50 mg |
| Xanthan gum | 20 mg |
| Maize starch | 93.8 mg |
| Lactose | 81.5 mg |
| Microgranular cellulose | 300 mg |
| Reticulated polyvinylpyrrolidone | 100 mg |
| Magnesium stearate | 10 mg |
| Hydroxypropylmethylcellulose | 14 mg |
| Polyethylene glycol 6000 | 0.8 mg |
| Titanium dioxide | 3.2 mg |
| Talc | 3.2 mg |
| Hydroxypropylmethylcellulose phthalate | 32 mg |
| Acetylated monoglycerides | 3.2 mg |

The tablets are prepared as in example 5 by using 220 g of lyophilisate prepared according to example 3.

We claim:

1. A pharmaceutical composition for oral use in unit dosage form which consists of a) a coating, b) a non-coated portion, and c) a non-protective first coating, said non-coated portion b) comprising a lyophilizate, said lyophilizate consisting of 25-500 mgs by weight of a glycosaminoglycan, 5-100 mgs by weight of at least one thickening agent, 25-500 mgs by weight of at least one surfactant, said glycosaminoglycan being a member selected from the group consisting of heparin of molecular weight between 6,000 and 30,000 Daltons and alkaline and alkali-earth salts thereof, fractions of low molecular weight heparin of molecular weight between 1,500 and 8,000 Daltons, low molecular weight fractions of dermatan sulfate of average molecular weight between 2,000 and 8,000 Daltons and glucuronylglycosaminoglycan sulfate known as sulodexide (INN), said coating a) consisting of a gastroresistant enterosoluble film in the amount of 2-10% by weight with respect to said non-coated portion b), said non-protective first coating c) being interposed between said lyophilizate and said gastroresistant enterosoluble film and being obtained by spraying a suspension of 3.5-21 mgs of hydroxypropylmethylcellulose, 0.2-1.2 mgs of polyethylene glycol 6000, 0.8-4.8 mgs of titanium dioxide and 0.8-4.8 mgs of talc in a 22:1 mixture of 95% ethyl alcohol and water, in such an amount that the weight of said non-protective first coating c) is between 1% and 5% as to the weight of said non-coated portion b).

2. The pharmaceutical composition according to claim 1 wherein said non-coated portion b) comprises a lyophilizate, said lyophilizate consisting of 200 mgs of low molecular weight dermatan sulfate of average molecular weight 5,600 Daltons, 20 mgs of sodium alginate, 100 mgs of saccharose monopalmitate, and 50 mgs of sodium lauryl sarcosinate, said coating a) being a gastroresistant enterosoluble film consisting of 24 mgs hydroxypropylmethylcellulose phthalate and 2.4 mgs of acetylated monoglycerides, said non-protective coating c) consisting of 10.5 mgs of hydroxypropylmethylcellulose, 0.6 mgs polyethylene glycol 6000, 2.4 mgs. of titanium dioxide and 2.4 mgs. of talc.

3. The composition according to claim 1 which is in the form of tablets, capsules.

4. The composition according to claim 1 wherein said gastroresistant enterosoluble film consists of at least one member selected from the group consisting of copolymers of the methacrylic acid and of the methacrylic esters in different ratios known as Eudragit ®, polyvinylacetophthalate and hydroxypropylmethylcellulose phthalate and at least one plasticizer which is a member selected from the group consisting of diethylphthalate, triacetin, polyethylene glycols and acetylated monoglycerides, said plasticizer being in the amount of 5-15% by weight of said gastroresistant enterosoluble film.

5. The composition according to claim 1 wherein said thickening agent is at least one member selected from the group consisting of gum arabic, gum tragacanth, xanthan gum, pectins, starch, carrageenans, alginates, casein, gelatin, hydroxyethylcellulose, methylcellulose, hydroxypropylcellulose, carboxymethylcellulose, polyvinylpyrrolidone, polyvinyl alcohol, carboxyvinyl polymers known as Carbopol ®, hydrogenated castor oil and aluminum oxide monostearate.

6. The composition according to claim 1 wherein said surfactant is at least one member selected from the group consisting of sodium cholate, sodium glycholate, sodium taurocholate, sodium laurylsarcosinate, egg lecithin, soya beam lecithin, saccharose monopalmitate and polysorbates known as Tween ®.

7. The composition according to claim 1 wherein said heparin is sodium heparin having an anticoagulant activity equal to 168 I.U./mg, said low molecular weight heparin has average molecular weight equal to 4500 Daltons and anticoagulant activity equal to 46 USP/mg and 202 I.U. AXa/mg, said glucuronylglycosaminoglycan sulfate has a title equal to 37 I.U. APTT/mg and to 82 I.U. AXa/mg, said low molecular weight dermatan sulfate has an average molecular weight equal to 5600 Daltons and a title equal to 1.4 I.U. APTT/mg and to 10 I.U. AXa/mg.

8. The composition according to claim 7 wherein said lyophilizate contains 100 mgs of xanthan gum, 250 mgs of saccharose monopalmitate, 250 mgs of sodium laurylsarcosinate and 500 mgs of glucuronylglycosaminoglycan sulfate or 500 mgs of sodium heparin.

9. A pharmaceutical composition for oral use in unit dosage form which consists of a) a coating, b) a non-coated portion, c) a non-protective first coating, and d) a sugar coating said non-coated portion b) comprising a lyophilizate, said lyophilizate consisting of 25–500 mgs by weight of a glycosaminoglycan, 5–100 mgs by weight of at least one thickening agent, 25–500 mgs by weight of at least one surfactant, said glycosaminoglycan being a member selected from the group consisting of heparin of molecular weight between 6,000 and 30,000 Daltons and alkaline and alkali-earth salts thereof, fractions of low molecular weight heparin of molecular weight between 1,500 and 8,000 Daltons low molecular weight fractions of dermatan sulfate of average molecular weight between 2,000 and 8,000 Daltons and glucuronylglycosaminoglycan sulfate known as sulodexide (INN), said coating a) consisting of a gastroresistant enterosoluble film in the amount of 2–10% by weight with respect to said non-coated portion b), said non-protective first coating c) being interposed between said lyophilizate and said gastroresistant enterosoluble film and being obtained by spraying a suspension of 3.5–21 mgs of hydroxypropylmethylcellulose, 0.2–1.2 mgs of polyethylene glycol 6000, 0.8–4.8 mgs of titanium dioxide and 0.8–4.8 mgs of talc in a 22:1 mixture of 95% ethyl alcohol and water, in such an amount that the weight of said non-protective first coating is between 1% and 5% as to the weight of said non-coated portion and d) a sugar coating externally to said coating a).

* * * * *